United States Patent [19]
Cunningham

[11] Patent Number: 5,340,376
[45] Date of Patent: Aug. 23, 1994

[54] CONTROLLED-RELEASE MICROBE NUTRIENTS AND METHOD FOR BIOREMEDIATION

[75] Inventor: John Cunningham, Tracy, Calif.

[73] Assignee: The Sierra Horticultural Products Company, Milpitas, Calif.

[21] Appl. No.: 793,355

[22] PCT Filed: Jun. 6, 1991

[86] PCT No.: PCT/US91/03986

§ 371 Date: Jan. 8, 1992

§ 102(e) Date: Jan. 8, 1992

[87] PCT Pub. No.: WO92/19544

PCT Pub. Date: Nov. 12, 1992

Related U.S. Application Data

[63] Continuation-in-part of Ser. No. 535,393, Jun. 8, 1990, abandoned.

[51] Int. Cl.$^5$ .................. C05F 11/08; C05F 3/00
[52] U.S. Cl. .................. 71/6; 71/64.11; 71/903; 210/610; 435/262
[58] Field of Search .......... 71/903, 64.11, 6–8; 210/610, 611; 435/262

[56] References Cited

U.S. PATENT DOCUMENTS

| | | | |
|---|---|---|---|
| 3,232,739 | 2/1966 | Belak | 71/28 |
| 3,252,786 | 5/1966 | Bozzelli et al. | 71/64.07 |
| 3,259,482 | 7/1966 | Hansen | 71/64.11 |
| 3,300,293 | 1/1967 | Bozzelli et al. | 71/28 |
| 3,475,154 | 10/1969 | Kato et al. | 71/64.07 |
| 3,846,290 | 11/1974 | Raymond | 210/610 |
| 3,943,066 | 3/1976 | Fusey | 252/356 |
| 3,952,741 | 4/1976 | Baker | 424/405 |
| 4,035,289 | 7/1977 | Guillerme et al. | 210/610 |
| 4,111,201 | 9/1978 | Theeuwes | 424/473 |
| 4,120,685 | 10/1978 | Vargiu et al. | 71/30 |
| 4,210,437 | 7/1980 | Windgassen et al. | 71/28 |
| 4,401,569 | 8/1983 | Jhaveri et al. | 210/610 |
| 4,401,762 | 8/1983 | Tellier et al. | 435/252.1 |
| 4,460,692 | 7/1984 | Tellier et al. | 435/248 |
| 4,493,895 | 1/1985 | Colaruotolo et al. | 435/262 |
| 4,563,208 | 1/1986 | Backlund | 71/28 |
| 4,581,846 | 4/1986 | Stensaas | 71/64.11 |
| 4,657,576 | 4/1987 | Lambie | 71/64.07 |
| 4,727,031 | 2/1988 | Brown et al. | 435/244 |
| 4,756,738 | 7/1988 | Detroit | 71/27 |
| 4,849,360 | 7/1989 | Norris et al. | 435/264 |
| 4,871,673 | 10/1989 | Rehm et al. | 435/262 |
| 4,925,802 | 5/1990 | Nelson et al. | 435/262 |

FOREIGN PATENT DOCUMENTS 0027694 4/1981 European Pat. Off. .

OTHER PUBLICATIONS

*Genetic Engineering News* (Nov./Dec. 1989) 9(10):3.
Busch, *Aerobic Biological Treatment of Waste Waters*, Oligodynamics Press, Houston, (1971) pp. 107–111.

*Primary Examiner*—Ferris Lander
*Attorney, Agent, or Firm*—Morrison & Foerster

[57] ABSTRACT

A controlled-release nutrient source is added at a low level to a bioremediation environment to enhance microorganism growth and activity and promote the effectiveness of the bioremediation in removing environmental contaminants.

19 Claims, 6 Drawing Sheets

CONTROLLED-RELEASE MICROBE NUTRIENTS AND METHOD FOR BIOREMEDIATION

This application is a continuation-in-part of U.S. Ser. No. 535,393, filed Jun. 8, 1990 and abandoned on Jan. 9, 1992.

FIELD OF THE INVENTION

This invention relates to improvements in biological remediation (bioremediation) efficiencies and improvements to the environmental soundness of the bioremediation approach to contamination cleanup. More particularly, it relates to improved nutrient delivery systems which reduce nutrient losses in open systems such as the ones found in most bioremediation operations. These nutrient delivery systems are amenable to both soil and water applications and are particularly helpful in reducing labor costs associated with nutrient application and also in reducing the potential for environmental damage due to nutrient run-off.

BACKGROUND INFORMATION

Bioremediation refers to the conversion of toxic environment contaminating compounds into innocuous substances by way of microbial digestion. Bioremediation has been successfully used to treat contaminated soil in above-ground treatment systems, above-ground slurry bioreactors, slurry pits, above-ground soil heaps, composting material, and in situ. A good example of in situ soil treatment came following the Exxon Valdez oil spill in Prince William Sound, Alaska. This oil contaminated miles of Alaskan shoreline and an approximately 70 mile section of shoreline was treated using bioremediation. This remediation process as it was employed focused on enhancing the indigenous microorganisms' growth and oil degrading activities through the application of nutrients.

Representative disclosures of bioremediation process include U.S. Pat. No. 4,035,289, to Michel Guillerme et al., which discloses a method for removing hydrocarbon residues from the effluents from oil well drilling. This method involves culturing microorganisms in a portion of the effluent and then adding the portion back to the remainder to degrade the hydrocarbons. *Genetic Engineering News*, vol. 9, No. 10 (Nov.–Dec. 1989) at page 3 presents a good example of the in situ bioremediation processes used to assist the clean-up of the Exxon Valdez oil spill in Prince William Sound, Alaska.

It is known that speeding the bioremediation process, by promoting the growth and activity of the waste-degrading microorganisms is desirable. In most situations the microorganisms naturally present in the soil and groundwater are capable of degrading the contaminating compounds. For a successful remediation, the bioremediator must enhance the growth and activity of these naturally occurring microorganisms. To that end, it is understood that supplying the microorganisms with nutrients and advantageous environmental conditions is beneficial. Just noted U.S. Pat. No. 4,035,289 teaches the addition of nitrogen and phosphorus sources to its culturing medium. U.S. Pat. No. 4,727,031 to Richard A. Brown et al., describes a composition of nutrients and a method of using the composition to stimulate the growth of aerobic bacteria, and particularly bacteria capable of hazardous waste degradation. This patent makes reference to Busch, *Aerobic Biological Treatment of Waste Waters*, Oligodynamics Press, Houston (1971), at page 107, for teaching that phosphorus and nitrogen are critical growth-limiting nutrients and when not present must be added to aerobic bacteria, such as those found naturally occurring in soil and water environments. Other similar disclosures of bioremediation include U.S. Pat. No. 3,846,290 to Richard Raymond, which discloses the advantageous injection of nutrients into subsurface water supplies to reduce contaminating hydrocarbons; U.S. Pat. No. 4,401,569 to Vidyut Jhaveri et al., which similarly shows injecting nutrients into the ground to enhance microbial action on contaminants; U.S. Pat. No. 4,925,802 to Michael Nelson et al., which shows adding an amino acid to bioremediation systems; U.S. Pat. No. 4,849,360 to Edward Azarowicz, which shows a multitank digestion process for degrading oily wastes; and U.S. Pat. No. 4,493,895 to Joseph F. Colaruotolo et al., which shows particular microorganisms which are capable of dissimilating halogenated compounds into the natural carbon cycle.

In general, therefore, bioremediations are speeded by adding nutrients, pH adjusters, and if aerobic microorganisms are used, oxygen to the soil and/or water of interest. By adjusting these parameters the indigenous microorganisms will multiply and become more active resulting in faster waste degradation. It only becomes necessary to add "foreign" microorganisms to the contaminated environment if the indigenous microorganisms do not posses the genes needed to create the enzymes necessary to degrade the contaminant, if the contaminant is at such a high concentration as to be toxic to the natural microorganisms, or if the contaminant concentration is so low the natural level of microorganisms cannot further degrade it to an acceptable level.

In most cases, bioremediations are performed in environments such as on site locations which can be classified as open systems. In the case of biodegradation in a closed environment, such as a batch bioreactor, it is sufficient to use an aqueous culture medium which completely and immediately supplies the microorganisms with the various nutrients required to increase degradation rates. These various nutrient elements are discussed in U.S. Pat. Nos. 4,035,289 and 4,727,031 which were noted above. Nutrient needs in open systems cannot be efficiently filled using the teachings of U.S. Pat. No. 4,035,289. This is because this patent shows the application of nutrient compounds which have virtually no ability to remain in the microorganisms' environment for extended periods in an open system. In this situation, it is necessary to apply these nutrients repeatedly to the open system throughout the remediation's duration.

The resulting depletion-reapplication cycle puts the microorganisms in a stressed state, and the microbes degradative efficiency is reduced. In addition, the washing away of the nutrients, from the point of application, is wasteful and may actually add to the environmental problem. One example of a nutrient runoff problem is blue baby syndrome which is caused by nitrates contaminating "potable" water supplies. This nutrient loss may be avoided to some extent by supplying nutrients in a form which can be associated or bound with the contaminant, such as a hydrocarbon waste, to provide a localized growth medium for the microorganisms.

U.S. Pat. No. 3,943,066, to Pierre Fusey, discloses a method for nutrient-waste mass association using an aqueous biodegradable emulsion of nitrogen- and phosphorus-containing substances with the hydrocarbon waste. In U.S. Pat. No. 4,460,692, to Jacques Tellier et al., a lipophilic microemulsion of an aqueous nutrient solution is applied in a layer upon the waste mass. These methods provide a way to associate essential nutrients onto the surface of the organic waste, but do not provide a controlled rate of nutrient release to the microorganisms' environment. In another, related disclosure, U.S. Pat. No. 4,401,762, also to Jacques Tellier et al., describes a process of culturing microorganisms using a microemulsion of nutrients and the use of this process in biodegradation settings.

The present invention addresses the problem of nutrient delivery to bioremediation environments by using controlled-release nutrient delivery systems engineered specifically for microorganisms. Controlled-release compositions have been used heretofore to provide nutrients to growing organisms, such as plants. See, for example, U.S. Pat. No. 4,657,576 to Johannes Lambie, which discloses a fertilizer composition for releasing nutrients to plants throughout the growing season; U.S. Pat. Nos. 3,300,293 and 3,252,786 to Andrew Bozzelli et al., which each relate to a slow-release fertilizer composition comprising a dispersion of urea-wax adduct in wax and its use fertilizing crops; U.S. Pat. No. 3,259,482 to Louis Hansen, which describes a slow-release fertilizer having a plurality of epoxy-polyester resin coatings and its use with plants; U.S. Pat. No. 3,232,739 to Steven Belak, which describes a polyurethane foam extended with free urea and the ability of the foams to supply urea fertilization to a plant throughout a long period of time; U.S. Pat. No. 3,252,786 to Andrew Bozzelli et al., which involves slow-release fertilizer compositions containing urea, wax, rosin, and optionally asphalt, and their use in fertilization processes; U.S. Pat. No. 3,475,154 to Haruhiro Kato et al., which describes resin-coated fertilizer particles and their use in garden settings; U.S. Pat. No. 4,120,685 to Silvio Vargiu et al., which describes fertilizers capable of achieving slow-release of nitrogen from urea-formaldehyde mixtures; U.S. Pat. No. 4,563,208 to Peter Backlund, which shows that fertilizer particles can be covered with a reaction product of urea and metal oxides; U.S. Pat. No. 4,210,437 to Robert Windgassen et al., which shows liquid fertilizer compositions which provide sulfur, nitrogen and micronutrient metals; and U.S. Pat. No. 4,756,738 to William J. Detroit, which shows a copolymer matrix which is capable of gradually releasing fertilizer.

Additional patents of note are U.S. Pat. No. 4,111,201, to Felix Theeuwes, and U.S. Pat. No. 3,952,741, to Richard Baker, which discloses devices capable of osmotically delivering beneficial agents. While for the most part, these patents are directed to delivering pharmaceutical agents to patients, they do generally include the delivery of any "active agent", including in the case of U.S. Pat. No. 4,111,201 microorganism attenuators, fermentation agents, nutrients and other agents that "benefit the environment of use" and in the case of U.S. Pat. No. 3,952,741, any agent in any way affecting any biological entity.

The current invention improves the efficiency of bioremediations in soil and/or aqueous environments by providing controlled-release compositions which supply nutrients to the microorganisms in a regulated, environmentally sound, and cost effective manner.

STATEMENT OF THE INVENTION

An improvement in bioremediation processes has now been found. Such bioremediation processes are those in which an organic chemical-contaminated soil or aqueous environment is remediated by the digestive action of microorganisms, on the chemical contaminant, within the environment. This digestive action typically takes two or more months before acceptable levels of degradation have taken place and the contaminated environment is no longer considered a threat. The improvement provided by the present invention involves applying to said environment, and thus the degrading microorganisms present therein, a controlled-release source of microorganism nutrients at a low level and optionally vitamins and/or nutrients which double as buffering agents (to keep the environment surrounding the product at a pH which is compatible with the growth and activity of the desired microorganisms). This controlled-release source is capable of continuously supplying an effective level of microorganism-promoting nutrients, some of which may double as buffering agents, to the contaminated environment during the prolonged period of digestive action. These prolonged periods of bioremediation action are those typically associated with this process in the art, such as at least about 1 week and more commonly from 1 to 100 weeks, especially from 10 to 40 weeks. The controlled-release source of nutrients typically releases nitrogen and/or phosphorus and/or sulfur to the microorganisms. This invention can find application in bioremediations performed in soils and/or aqueous environments which have become contaminated with aliphatic hydrocarbons. It can also find use in soils and/or aqueous environments which have been contaminated with aromatic hydrocarbons, including halogenated aromatic, polynuclear aromatic, polychlorinated biphenyls (PCB), trichloroethylene (TCE), percholorethylene, various pesticides, various herbicides, and with any chemical deemed to be bioremediable.

The invention can be used in soil environments and in aqueous environments. These environments can be open or closed. The soil environments include soil in above-ground treatment systems, above-ground slurry bioreactors, slurry pits, above-ground soil heaps, composting material, in situ, and the like. The aqueous environments include lakes, ponds, rivers, slurry pits, above-ground slurry bioreactors, bioreactors, ground water, and the like.

In addition to the macronutrients (nitrogen, phosphorus, and sulfur), the invention can serve to deliver essential micronutrients such as micronutrient metals to the microorganisms as well. In another embodiment additional growth promoters, a vitamin source, for example yeast extract, can be incorporated into the controlled-release composition or administered concomitantly to additionally promote the vitality and growth of the microorganisms. Thus, in additional aspects, this invention can deliver in a controlled-sustained manner macronutrients, micronutrients, buffers, vitamins and the like or any combination thereof, to the bioremediation microorganisms.

In a preferred embodiment, this invention provides significantly enhanced levels of bioremediation by the unexpected feature of using lower levels of nutrients—that is, lower use levels of nutrients at sustained levels give higher activity than is achieved at higher nutrient levels.

As will be apparent, the present invention is highly advantageous when applied to environments requiring bioremediation activities in that it provides a way to efficiently deliver essential nutrients, in an environmentally sound way, to the waste-degrading microorganisms throughout the entire remediation without the expensive, wasteful, labor intensive multiple reapplications called for in methods of the prior art. Surprisingly, in order to obtain the most efficient bioremediation, the concentration of the nutrients in the soil is maintained at a lower level than suggested by the prior art.

BRIEF DESCRIPTION OF THE DRAWINGS

This invention will be described with reference being made to the accompanying drawings in which.

DESCRIPTION OF PREFERRED EMBODIMENTS

The Macronutrients

Figure 1:
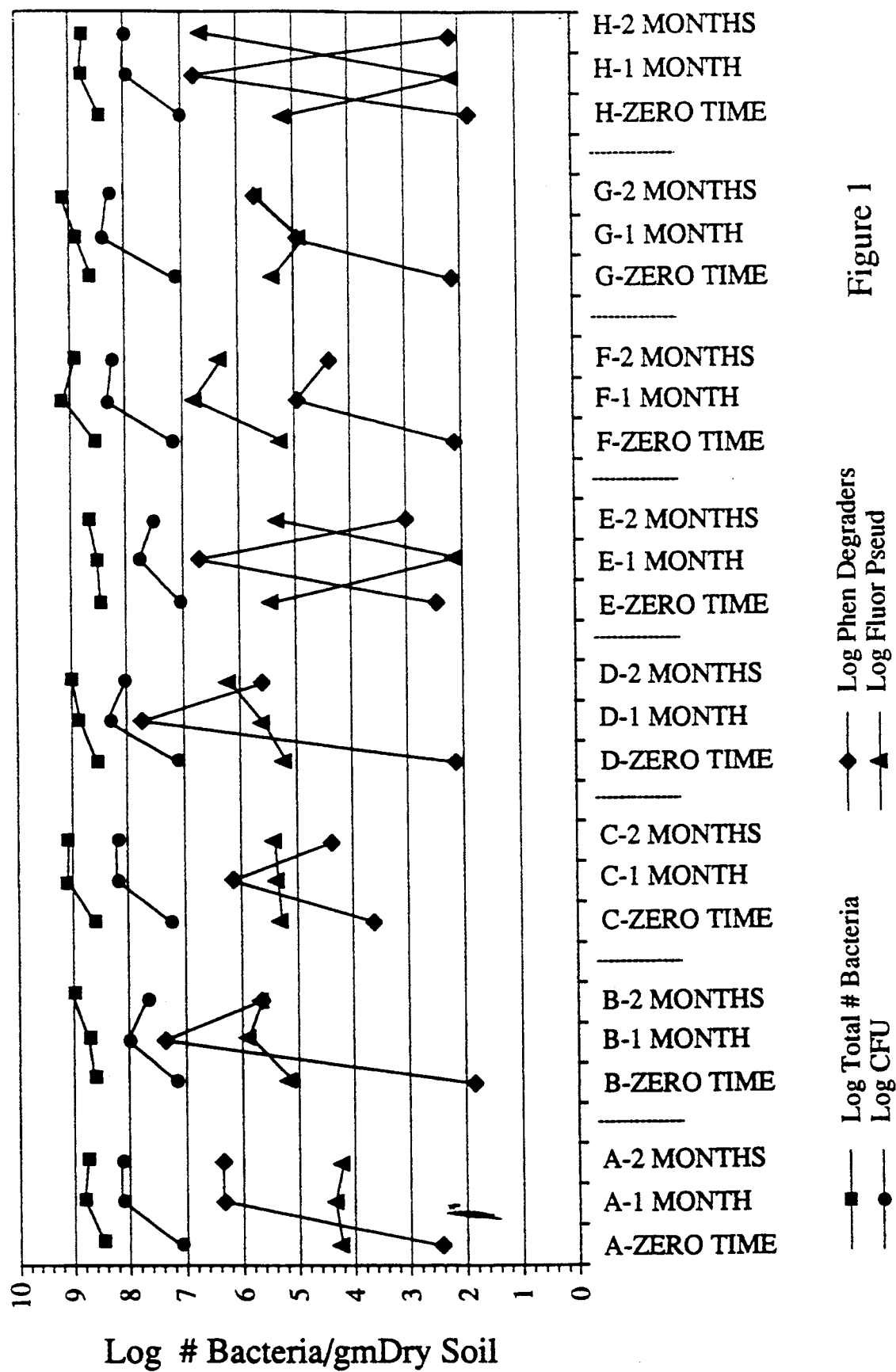
FIG. 1 is a graph showing bacterial levels in soil over time at various levels and types of nutrient addition in accord and not in accord with this invention.

The materials employed in the present invention deliver nitrogen, phosphorus, and/or sulfur as macronutrients to the bioremediation microorganisms. Nitrogen can be delivered as nitrate, ammonium, urea or cyanamide. Phosphorus is typically delivered as phosphate. Sulfur is generally delivered as sulfate. Potassium, a usual component of plant nutrient material, may be present but generally is not required. The macronutrients employed to make up the controlled-release product are normally standard fertilizer materials and can include urea, ammonium nitrate, ammonium phosphates, ammonium sulfate, calcium nitrate, calcium cyanamide, sodium nitrate, calcium phosphates, single superphosphate, triple superphosphate, potassium nitrate, and potassium sulfate. These materials are highly water soluble with the exception of calcium cyanamide and calcium phosphates, and if employed without a controlled-release coating, would rapidly dissolve in and be dissipated in an open environment. The amounts of nitrogen, phosphorus, and sulfur can be varied in the product to give compositions having from 0 to 40 percent nitrogen, from 0 to 40 percent phosphorus, and from 0 to 20 percent sulfur by weight based on the overall micronutrient composition. Preferred ranges are from 10 to 40 percent nitrogen and 2 to 20 percent phosphorous and 0 to 10 percent by weight sulphur. In one preferred embodiment, the total nitrogen is approximately 28 percent nitrogen, and the phosphorous level is 3.5 percent or 8 percent in $P_2O_5$ form. This type of product would be referred to as a 28-8-0 (0 being potassium in $K_2O$ form) product in typical fertilizer nomenclature. At this time, it is accepted in the bioremediation industry that the product should release 1 to 10 parts nitrogen per part by weight phosphorus.

Micronutrients

The materials employed in the present invention may also contain micronutrients to promote the growth and activity of the microorganisms. These micronutrients can include all those materials known by those in the art to be essential to the microorganisms. These can include metals, for example, magnesium, iron, manganese, calcium, and the like. The micronutrients are optional, and if present, are present in very low levels of typically less than 1 percent and more likely less than 0.1 percent by weight, such as from 1 to about 500 ppm by weight. These materials can be made to release at the same rate as the macronutrients or faster than the macronutrients depending upon the needs of the microorganisms. A faster release can be attained by coating these materials on the outside of particles so that they are released at the first part of the release cycle.

Vitamins and Buffers

Since the microorganisms also utilize vitamins such as thiamine, folic acid, biotin, nicotinic acid, and the like, these can also be included into the controlled-release products. It has been shown that part per million concentrations, and in some cases a fraction of a part per million, of vitamins can drastically increase activities of the microorganisms and thereby increase speed of waste degradation. For this reason, from 0.01 to 100 ppm by weight of such vitamins may be included in the product.

Microorganisms also thrive best in particular pH ranges, such as from about 6.5 to 8, so a buffering system may also be added to the product to maintain the environment around the controlled-release particle at these desirable pHs. This buffering system can be made up of compounds which double as a nutrient source making the system even more desirable. For example, the phosphate phosphorous sources can provide buffering capacity into these desired pH ranges. Representative buffers are a 1:1 mixture of KOH and $KH_2PO_4$ and a 2:1 disodium phosphate and monopotassium phosphate mixture.

Controlled-Release Coating

The controlled-release compositions of this invention are particulate solid materials which comprise a water soluble core of the nitrogen and/or phosphorus and/or sulfur micronutrient source and optionally micronutrients and/or vitamins and/or buffers surrounded by a release rate-controlling coating. While any of the release rate-controlling membrane materials of the art, such as those included in the above-referenced Theeuwes or Baker patents can be used (these patents are incorporated herein by reference), it has been found in our work to be advantageous to use a resin formed from linseed oil and dicyclopentadiene (DCPD) copolymerized and bodied. Such a composition is employed commercially under the trademark "Osmocote", a trademark of Grace-Sierra Horticultural Products Company. This material is described in U.S. Pat. No. 3,223,518 and Dutch Patent No. 132,686, both of which are incorporated herein by reference. This "Osmocote" coating is advantageous due to its low cost and high effectiveness when used to create controlled-release products capable of lasting from one week to 100 weeks. A typical remediation will last from 10 to 40 weeks.

Variation on the linseed oil/dicyclopentadiene system replaces part of the linseed oil with soybean oil plus maleic anhydride and pentaerythritol. These materials all function equivalently. More specific examples of these materials include soybean oil at 60 to 65 percent and DCPD at 35 to 40 percent by weight; soybean oil at 35 to 40 percent by weight, linseed oil at 20 to 26 percent by weight and DCPD at 35 to 40 percent by weight; and soybean oil at 55 to 60 percent by weight, maleic anhydride at 2 to 5 percent by weight, pentaerythritol at 2 to 5 percent by weight and DCPD at 35 to 40 percent by weight.

Other types of controlled-release coatings which can achieve the desired controlled nutrient release to bioremediation environments include polyethylene, polypropylene, ethylene, propylene copolymer, ethylenevinyl acetate copolymer, vinylidene chloride, vinyl chloride, vinylidene chloride-vinyl chloride copolymer, and polystyrene. These materials are discussed in more detail in U.S. Pat. No. 4,369,055 which is incorporated by reference.

Controlled-Release Nutrients

The macronutrients employed in the present process are typically granular materials having grain sizes from about 0.1 to about 5 mm. These granules will be composed of any macronutrient, micronutrient, vitamin, and/or buffer previously mentioned or amenable to being granulated and will be coated with a resin layer. This coating will most likely be the linseed oil/DCPD copolymerized resin and will be applied to the granules and then heat cured onto the granules' surface creating a controlled-release film. The amount of this resin applied to the granules will range from 1 to 20 percent by weight (based on the weight of macronutrients) depending on the granules' shape and the required longevity of the product. The typical percent of resin used will be between 5 and 15 percent.

Product Use In Bioremediations

In accord with the process of this invention, the precise amount used will depend on the level of contamination being treated, the concentration of background nutrients, the percentages of nutrients in the controlled-release product of interest, and other conditions affecting the nutrient release.

Typical use levels for soil treatment will run from about 0.50 to about 50 pounds of controlled-release nutrients per cubic yard of contaminated soil. We have found, quite unexpectedly, that even though the release of nutrient is controlled and delayed, we get best results at lower overall use levels than we observed for non-controlled release (i.e., wholly soluble) materials. More specifically, while soluble materials give best results at about 5 or 10 pounds per cubic yard, so as to obtain a contaminant carbon:nitrogen:phosphorus atomic ratio of 100:20:1, we have obtained far better results using as little as 1 pound of controlled-release material per cubic yard of soil. On this basis we prefer to use 0.25 to 5 pounds per cubic yard and especially 0.5 to 3 pounds per cubic yard.

In soil environments, moisture must be present to allow the microorganisms to flourish. Moisture may be added if desired. The controlled-release product may be spread on the contamination and/or tilled into the contaminated soil. In the case of contaminated aqueous environments, use levels of from about 0.0005 to about 0.5 pounds per gallon are advantageous, again this is dependant upon the environmental conditions.

The environment being remediated can be the naturally occurring soil or aqueous environment. Alternatively it can be a modified environment wherein the modifications improve the rate or extent of bioremediation. In the case of soil environments, this can include turning over the soil, composting the soil, adding surfactant, or slurrying the soil in a water medium.

In the case of an aqueous environment, the natural environment can be groundwater, effluent from an industrial process or any other waste water source. The improvement can include holding the water in basins or ponds to assure adequate remediation time as well as other improvements known to the art of water treatment processing.

The bioremediation processes of this invention may rely upon the microflora present in situ at the contamination site and this is typically preferred. Alternatively microorganisms may be seeded into the contamination site and these added materials can include any of the organisms known in the art to affect contaminant degradation such as the Pseudonomids, Methylotrophic bacteria, Acinetobacter as well as a variety of anaerobic bacteria. It is not intended that his invention be limited to any particular type or family of organisms, including genetically engineered microorganisms.

EXAMPLES

The invention will be further illustrated with reference to the following examples. These examples are provided solely to illustrate ways of practicing the invention, and are not to be construed as limitations on the invention's scope, which is instead defined by the claims hereinafter appended.

EXAMPLE 1

A nitrogen and phosphorus nutrient granule in controlled-release form was prepared as follows. Granules each containing ammonium nitrate, 80%; ammonium phosphates, 12%; calcium phosphates, 5%; and inerts, 3% were screened to a Tyler mesh range of $-6$ to $+12$. This material was then coated with 7.4% by weight (basis finished product) of a linseed oil/DCPD copolymerized resin (6% w linseed oil/38% w DCPD). The coating was accomplished by heating the screened nutrient granules to approximately 70° C., then applying the resin at a flow rate which gives a uniform coating. This controlled-release material had a nitrogen content of approximately 28% and a phosphorus content of approximately 3.5%. The release characteristics of this product, as found in the laboratory, showed that the nutrients were released over a three month period at 70° F. The lab test consisted of statistically splitting 8 grams of the controlled-release product out of the bulk and placing it in a funnel containing approximately 200 ml of washed sand. The funnels were leached every seven days with water and the leachate analyzed for nutrients.

This material was applied to soil contaminated with diesel oil. It was predicted, using the old methodology of applying soluble nutrients, that the bioremediation would take four months. The contaminated soil was remediated in slightly over two months using this controlled-release product. This material was also applied to the beaches in Prince William Sound, Alaska, contaminated with oil from the Exxon Valdez, and supplied nutrients continuously to the indigenous microorganisms for approximately three months.

EXAMPLE 2

The preparation of Example 1 was repeated with the following changes. After applying the controlled-release resin, a dispersion containing micronutrients, vitamins, and a buffer was applied to the granules and cured. The cured dispersion consisted of 20% resin by weight with the remaining 80% consisting of phosphate buffer, magnesium, iron, potassium, manganese, molybdenum, thiamine, riboflavin, nicotinic acid, pantothenic acid, folic acid, biotin, choline, inositol, and protein. This dispersion was then overcoated with 0.5% (by weight of finished product) linseed oil/DCPD resin. Also coated with this dispersion and then overcoated was a urea substrate consisting of 25% urea granules coated with 11.1% resin and the remaining 75% urea coated with 13.8% resin. This added urea was then mixed with the micronutrient containing particles to comprise 20% by weight of total product and created a product containing approximately 29% nitrogen, and 3% phosphorus as well as micronutrients.

This product was tested in a laboratory microcosm competing against a dry soluble nutrient of comparable composition. At four weeks, the bacteria population in the controlled-release nutrient treated microcosm was an order of magnitude higher than the soluble nutrient treated microcosm and two orders of magnitude higher than the microcosm having no nutrient treatment.

EXAMPLE 3

The experiment of Example 1 is repeated with the following change. The linseed oil/DCPD resin is replaced, using, instead, a resin made from soybean oil, 57 percent; maleic anhydride, 2.5 percent; pentaerythritol, 2.5 percent; and dicyclopentadiene, 38 percent.

EXAMPLE 4

The experiment of Example 2 is repeated with the following change. The linseed oil/DCPD resin is replaced, using, instead, a soybean oil based resin as described in Example 3.

EXAMPLE 5

Nitrogen and phosphorus nutrient granules, in controlled-release form, are prepared as follows. Granules containing urea are screened to a Tyler mesh range of −6 to +12. Granules containing calcium phosphate, monobasic are also screened to a Tyler mesh range of −6 to +12. 22.6 pounds of the urea granules are heated to approximately 65 C. and 3.4 percent linseed oil/DCPD resin is applied. Then 7.8 more pounds of screened, uncoated urea is mixed into the 22.6 pounds of partially coated urea and the mix is brought up to approximately 65° C. After achieving this temperature, 6.1 percent linseed oil/DCPD resin is added by weight of substrate and resin. To conclude the coat 14.2 pounds of calcium phosphate, monobasic acid is added to the partially coated urea fractions and the temperature is brought up to approximately 70° C. Resin is applied at 5.7 percent on the total weight of the coated product. The final product contains 52.5 percent urea coated with 13.8 percent resin, 17.5 percent urea coated with 11.1 percent resin, and 30.0 percent calcium phosphate, monobasic coated with 5.7 percent resin. This product will supply nitrogen and phosphorus continuously, in a ration of 5 to 1 respectively, for three months in a moist environment kept at 20° C.

EXAMPLE 6

A bioremediation field trial was conducted to determine if controlled-release nutrients would enhance the degradation of diesel when compared to the standard practice of applying dry soluble nutrients. The results of the trial are presented in FIGS. 1–6.

The two controlled-release products were added at concentrations of 1, 5, and 20 lb/cu yard of soil. The first controlled-release product used is referred to as Customblen TM 24-89 and contains 27.5% nitrogen and 8% phosphorus in $P_2O_5$ form. The second controlled-release product used is referred to as Max Bac TM 2 and contains 26% nitrogen, 10.5% phosphorus in $P_2O_5$ format, and 0.65% potassium in $K_2O$ form. The controlled-release products were prepared as described in Example 1 and Example 2 with the modification that the dispersion was coated onto the substrate before the controlled-release membrane was applied.

Two controls were present, one having no nutrient addition and one having 3.5 lb/cu yard of a 30-9-0 soluble fertilizer with an analysis of 16% ammonium, 14% nitrate, 3.27% water-soluble phosphate P, and 3.93% citrate-soluble phosphate P.

The eight experimental conditions were identified as follows:

| | |
|---|---|
| No nutrients | A-series |
| Soluble farm at 3.5 lb/cu yard | B-series |
| Customblen TM 24-89 at 1 lb/cu yard | C-series |
| Customblen TM 24-89 at 5 lb/cu yard | D-series |
| Customblen TM 24-89 at 20 lb/cu yard | E-series |
| Max Bac TM 2 at 1 lb/cu yard | F-series |
| Max Bac TM 2 at 5 lb/cu yard | G-series |
| Max Bac TM 2 at 20 lb/cu yard | H-series |

Each of the eight samples (one for each set of experimental conditions) was run in triplicate 3'×3' plots. The pH of the test plots was held at 6.5–8.0 by adding calcium carbonate. Moisture was maintained uniform in that all the plots were treated identically and allowed to vary uniformly between 20–60% moisture during the tests. In each case, the initial concentration of contaminants in the soil was approximately 2500 mg diesel per Kg dry virgin soil. The test plots were troweled once per week to add oxygen.

Samples were taken at 0 elapsed time, 1 month later and 2 months later and analyzed for total bacteria, colony-forming units, phenanthrene degraders (known hydrocarbon degraders), and fluorescent Pseudonomids. The samples were also tested for levels of total hydrocarbon and individual hydrocarbon fractions by carbon number. Conductivity, as a measure of available nutrient concentrations, was also measured on each sample.

As shown in FIG. 1, it was observed that the total bacteria present in the samples remained relatively constant among all of the samples with the exception that the high use levels (20 lb/cu yard—series E and H) of controlled release products gave lower bacterial levels than the 1 lb/cu yard or 5 lb/cu yard series (series C, D and F, G). Similarly only modest differences were noted in colony-forming unit concentration but with better performance being seen with low controlled release nutrient levels than at high levels. There were major differences in levels of phenanthrene degrading bacteria among the 8 tests. The control with no added nutrient was as much as two orders of magnitude lower than the tests with nutrient. At high use levels (20 lb/cu yard—series E and H), the added fertilizer first boosted and then depressed the number of organisms observed. At low levels (1 and 5 lb/cu yard—series C, D, G and H) the number of such organisms elevated over time by as much as 2½ orders of magnitudes and in several samples as much as one order of magnitude greater than the standard practice addition of soluble fertilizer. In virtually all cases where nutrient was added, including the control, the level of fluorescent Pseudonomids went up dramatically in the first month and then fell in the second month.

Figure 2:
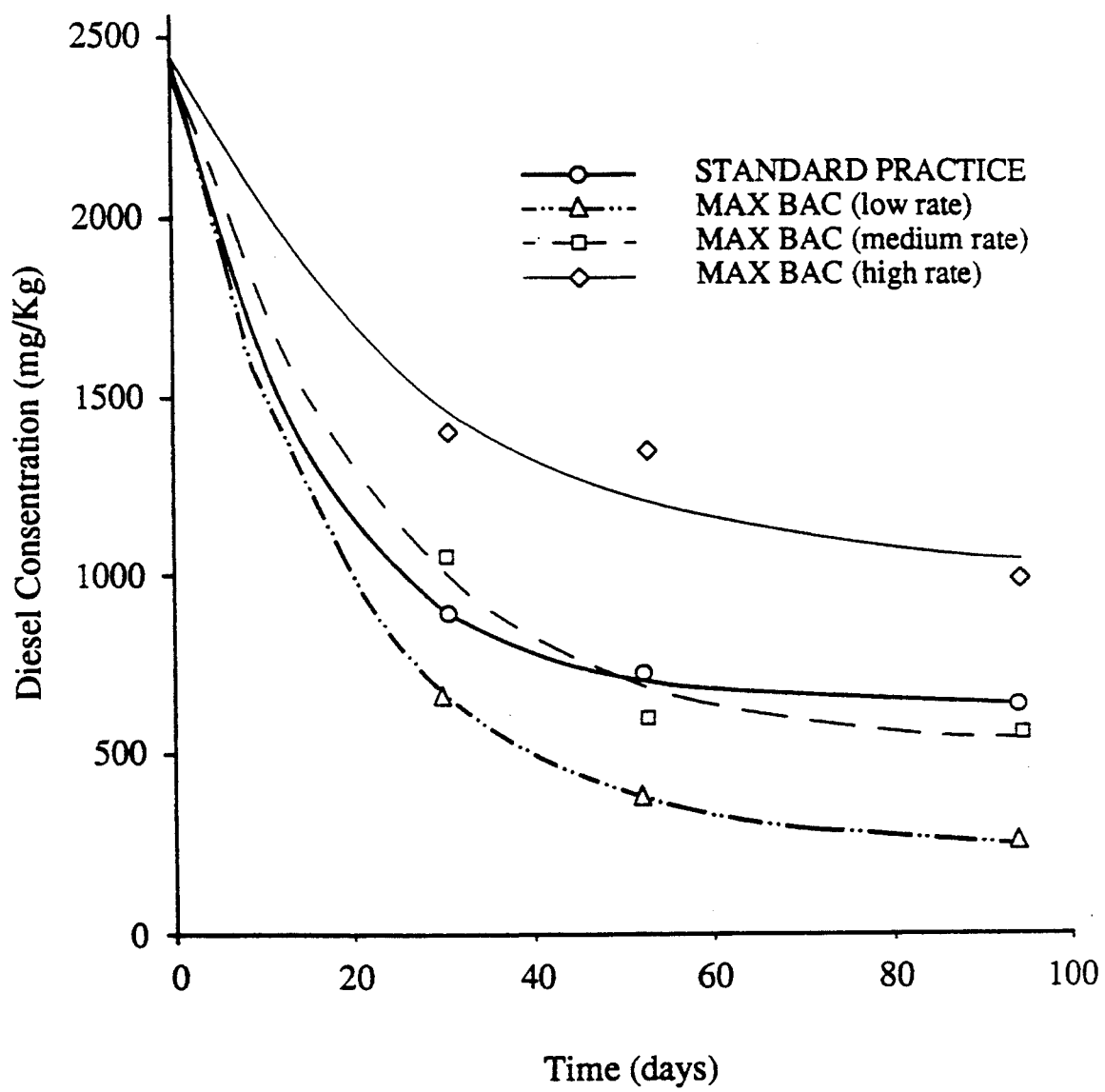
FIG. 2 is a three line graph showing diesel fuel contamination levels at various nutrient release rates in accord and not in accord with this invention over a 100-day trial period of bioremediation.
Figure 3:
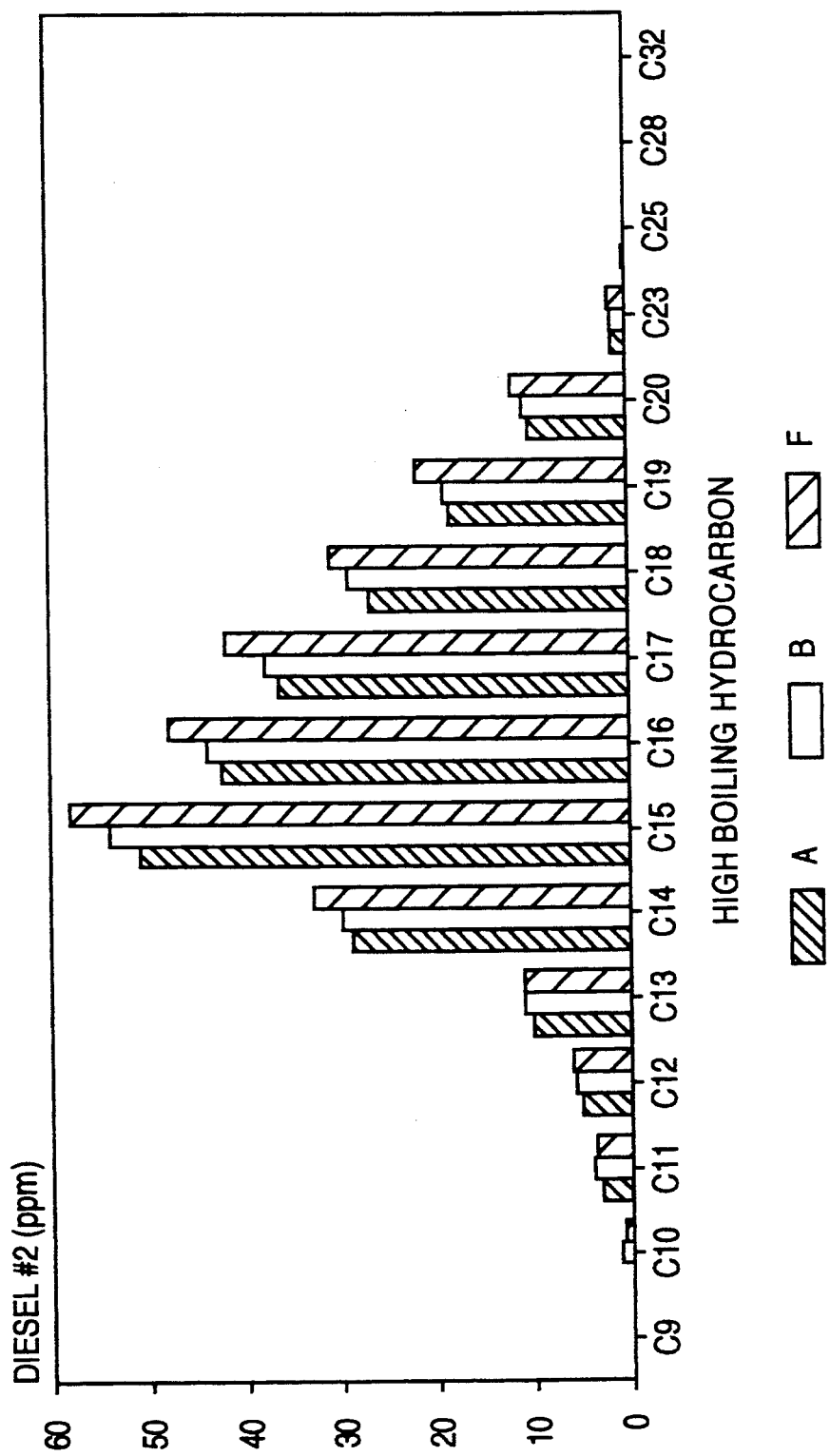
FIGS. 3-6 are a series of bar graphs comparing the levels of various hydrocarbon contaminants in an oil-fouled environment at a starting point (FIG. 3), after one month (FIG. 4), after about two months (FIG. 5), and after about three months (FIG. 6), when the present invention is practiced and when control conditions are imposed.
Figure 4:
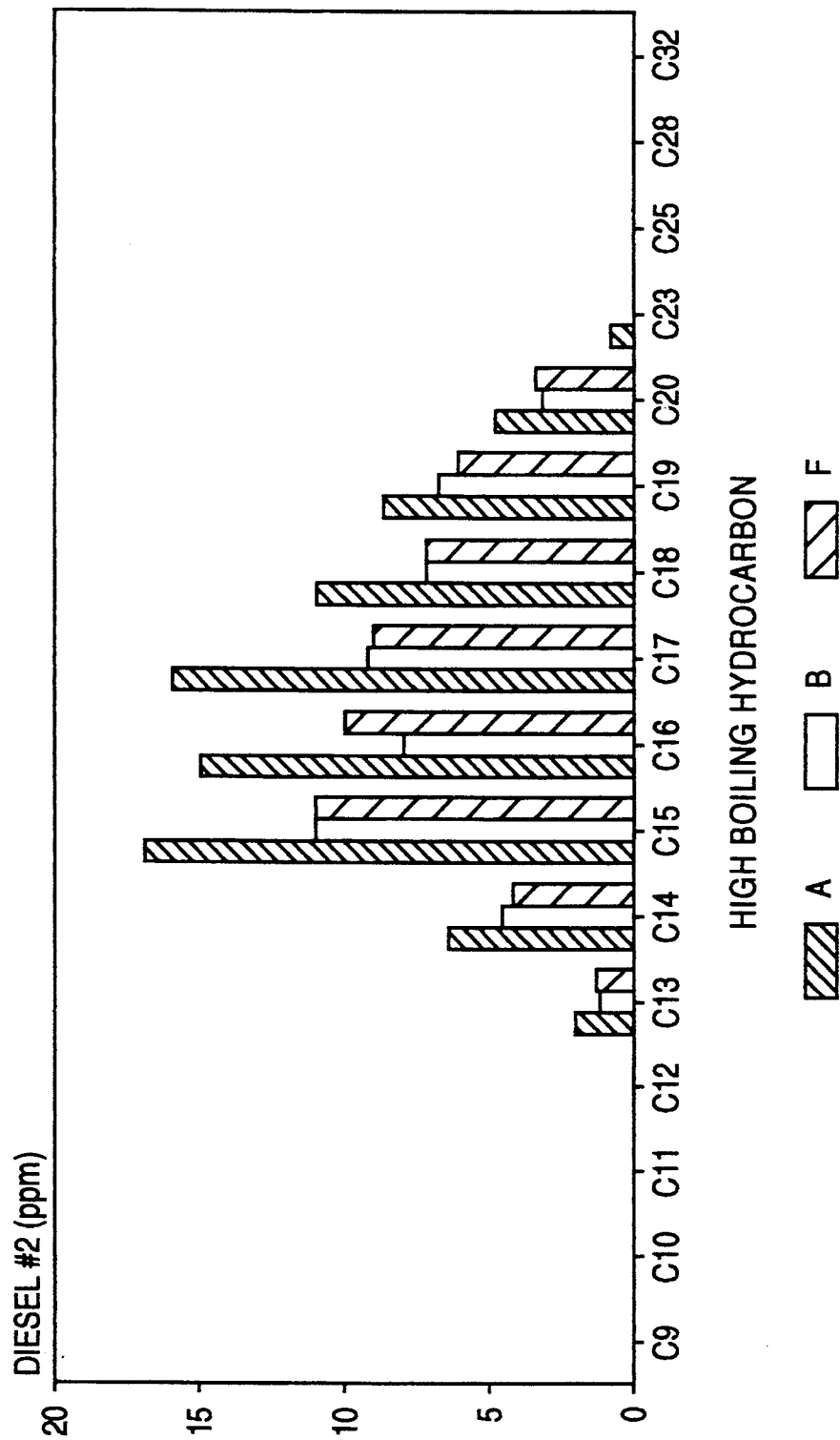
Figure 5:
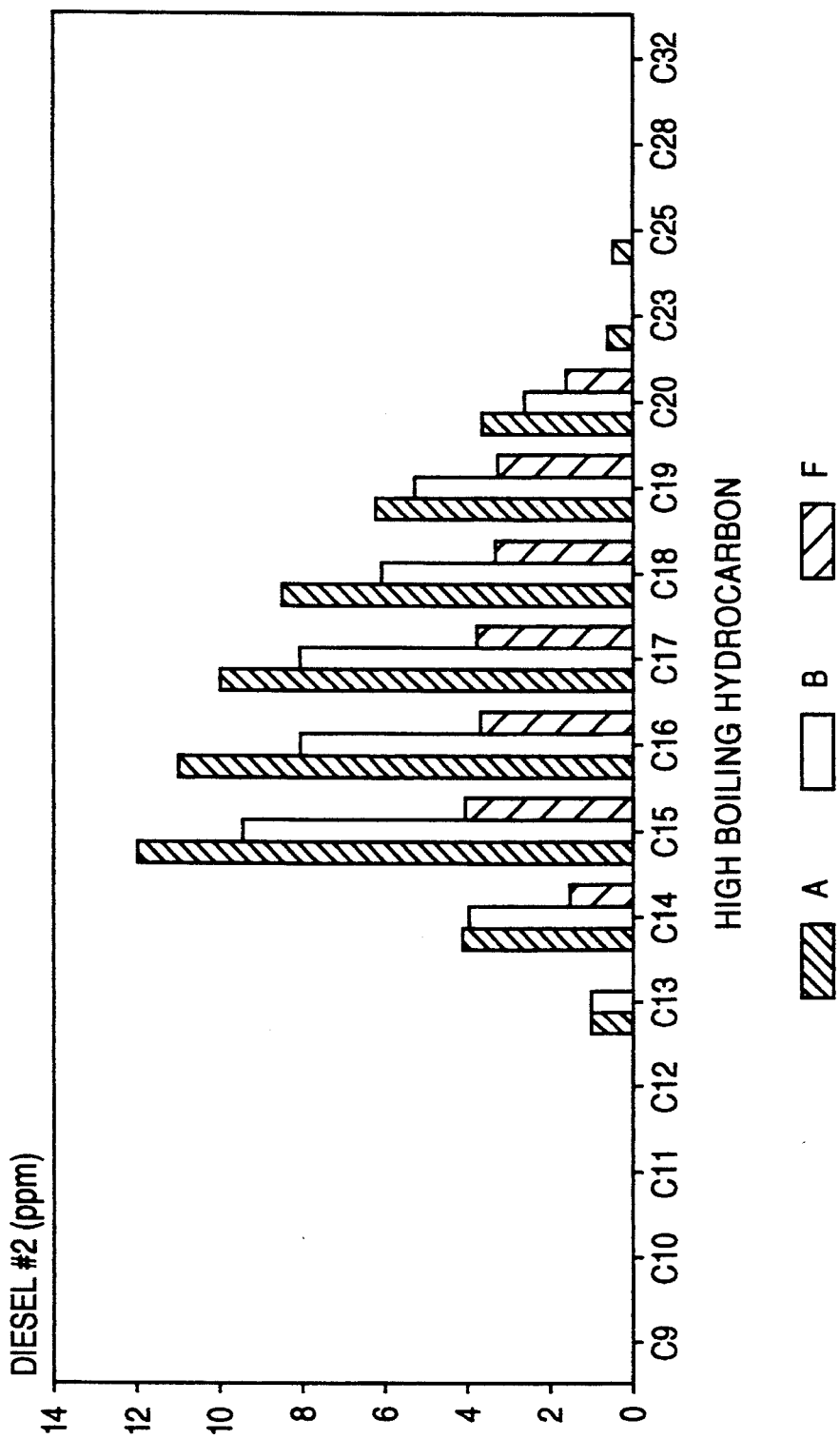
Figure 6:
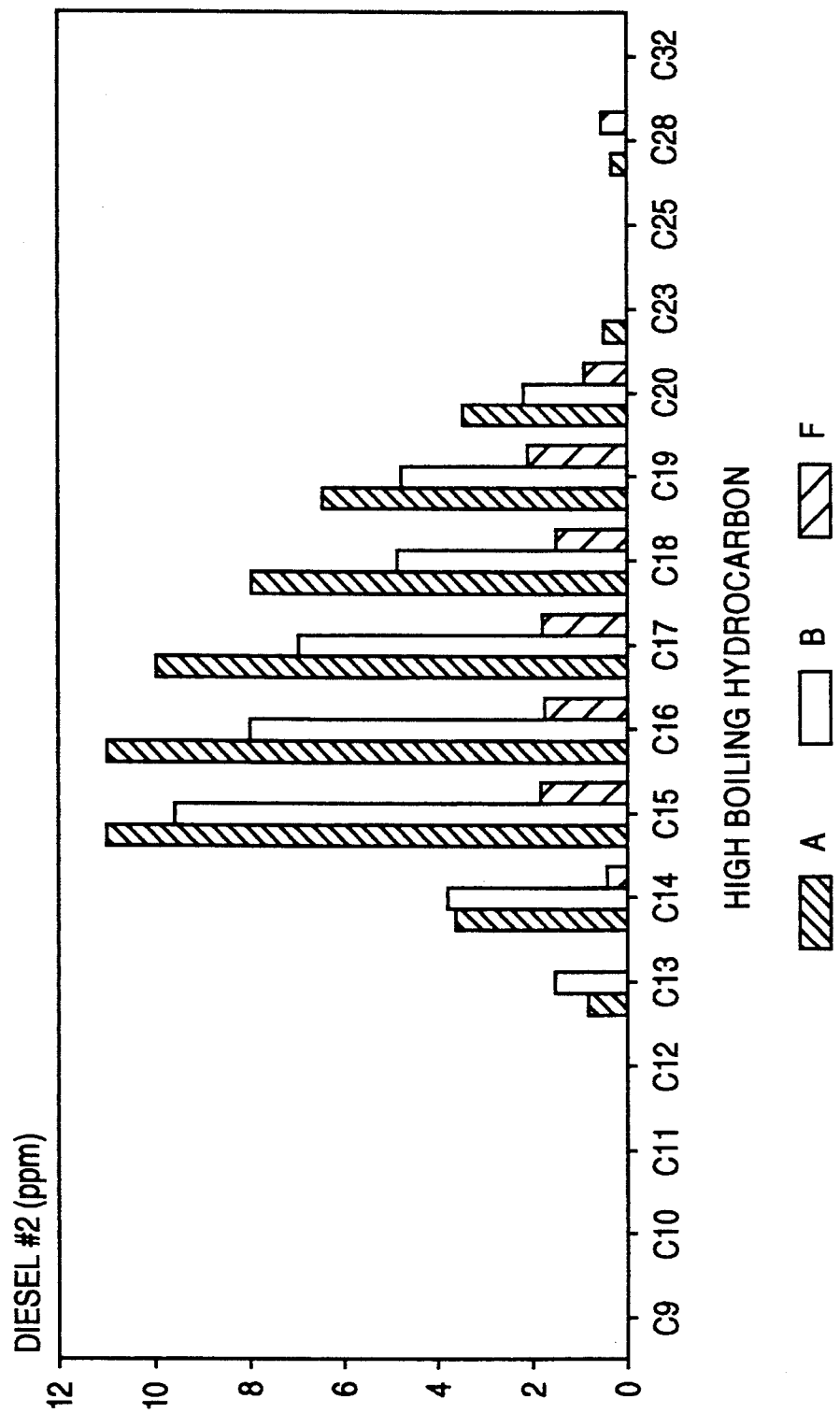

The actual bioremediation performance observed with these eight systems showed clearer advantages achieved by the present invention. In FIG. 2 the measured levels of total diesel contamination are plotted as a function of elapsed time.

The standard practice of adding dry soluble fertilizer reduced the contamination to about 750 ppm in 100 days. Interestingly, high loadings (20 lb/cu yard) of controlled release material gave poor results. At this condition, over 1000 ppm of contamination remained after 100 days. At a rate of 5 lb/cu yard, controlled release material reduced contamination to about 250 ppm in about 100 days. Best results were observed at the lowest rate of controlled release material addition—1 lb/cu yard. At this condition, the contamination was consumed the fastest and to the lowest level, 250 ppm.

Dirt samples initially containing added diesel contamination as noted above were bioremediated under 3 comparative conditions—condition A—no fertilizer, condition B—3.5 lb/cu yard of dry soluble fertilizer and condition F controlled release fertilizer at 1 lb/cu yard. Samples were taken at day 1, day 31, day 53, and day 95 and analyzed by gas chromatography. The results were digitized to give relative levels of each carbon number fraction. FIGS. 3, 4, 5 and 6 show the results of these analysis and illustrate a regular and striking advantage to the controlled release material which allowed the clean up to achieve a reduction in contamination to 16 units while the control was at 55 units and the soluble fertilizer test gave 41 units.

What is claimed:

1. In a biological remediation process wherein microorganisms are employed to degrade contaminating organic compounds present within an environment over an extended period of time, the improvement which comprises applying to said environment a low-level of controlled-release source of microorganisms nutrients capable of continuously supplying an effective microorganism growth-and activity-promoting level of nutrients to the microorganisms over a period of time of at least about two months, said controlled-release source of microorganism nutrients being in the form of coated solid particles each having a core of water soluble microorganism nutrients encapsulated in a release rate-controlling coating and where said particles are admixed in the environment at a level of 0.25 to 3 pounds per cubic yard of environment.

2. The process of claim 1 wherein said environment is a soil environment.

3. The process of claim 2 wherein said nutrients are applied to said soil in its natural environment.

4. The process of claim 2 wherein said soil is moved from its natural environment.

5. The process of claim 2 wherein said soil is mixed with a composting material.

6. The process of claim 2 wherein said soil is slurried in an aqueous environment.

7. The process of claim 1 wherein said environment is an aqueous environment.

8. The process of claim 7 wherein said aqueous environment is any naturally occurring body of water.

9. The process of claim 7 wherein said aqueous environment is any artificially formed body of water.

10. The process of claim 7 wherein said aqueous environment is groundwater.

11. The process of claim 7 wherein said aqueous environment is an effluent from an industrial process.

12. The process of claim 7 wherein said aqueous environment is municipal waste water.

13. The process of claim 1 wherein said nutrients comprise nitrogen and phosphorus.

14. The process of claim 13 wherein said nutrients additionally comprise sulfur.

15. The process of claim 13 wherein said nutrient additionally comprises micronutrients.

16. The process of claim 13 wherein said nutrients additionally comprise a vitamin.

17. The process of claim 13 wherein said nutrients additionally comprise a buffer.

18. The process of claim 13 wherein said controlled-release nutrients are comprised of water soluble macronutrients encapsulated in a linseed oil/dicyclopentadiene resin.

19. In a biological remediation process wherein microorganisms are employed to degrade contaminating organic compounds present within a soil environment over an extended period of time, the improvement which comprises admixing with said soil environment from about 0.25 to 3 pounds per cubic yard of soil environment of controlled-release source of microorganisms nutrients capable of continuously supplying an effective microorganism growth-and activity-promoting level of nutrients to the microorganisms over a period of time of at least about two months.

* * * * *